United States Patent
Walter et al.

(10) Patent No.: US 7,820,830 B2
(45) Date of Patent: Oct. 26, 2010

(54) PROCESS FOR THE PRODUCTION OF CARBOXANILIDES

(75) Inventors: Harald Walter, Basel (CH); Camilla Corsi, Basel (CH); Josef Ehrenfreund, Basel (CH); Hans Tobler, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 294 days.

(21) Appl. No.: 12/093,619

(22) PCT Filed: Nov. 13, 2006

(86) PCT No.: PCT/EP2006/010866

§ 371 (c)(1),
(2), (4) Date: Jun. 25, 2008

(87) PCT Pub. No.: WO2007/057140

PCT Pub. Date: May 4, 2007

(65) Prior Publication Data

US 2008/0262242 A1    Oct. 23, 2008

(30) Foreign Application Priority Data

Nov. 15, 2005   (EP)   ................. 05024969

(51) Int. Cl.
*C07D 231/14*   (2006.01)
(52) U.S. Cl. .................................. 548/374.1
(58) Field of Classification Search ........... None
See application file for complete search history.

(56) References Cited

FOREIGN PATENT DOCUMENTS

WO   03074491   9/2003
WO   2004039799   5/2004

*Primary Examiner*—Kamal A Saeed
(74) *Attorney, Agent, or Firm*—William F. Mulholland, II

(57) ABSTRACT

The present invention relates to a novel process for the preparation of a compound of general formula (I): wherein $R^1$ is H or $C_{1-4}$ alkyl and $R^2$ is difluoromethyl or trifluoromethyl, which comprises reacting a compound of general formula (II): wherein $R^1$ has the meaning given above and X is chloro or bromo, with a compound of general formula (III): wherein $R^2$ has the meaning given above, in the presence of a base, a palladium catalyst and a ferrocenyl biphoshine ligand of the Josiphos type, the reaction being carried out in an ether solvent at a reflux temperature of at least 100° C.

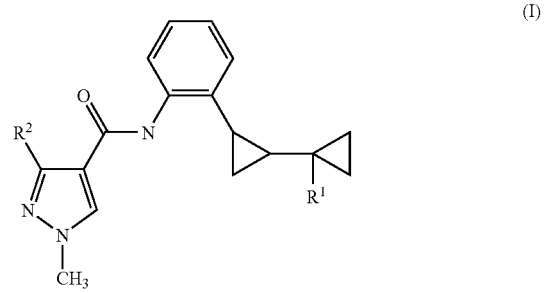

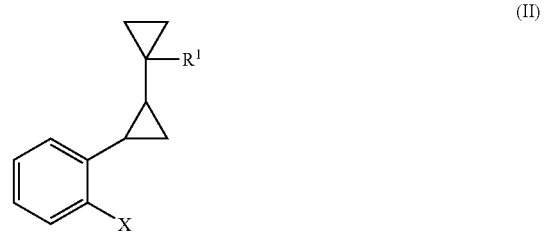

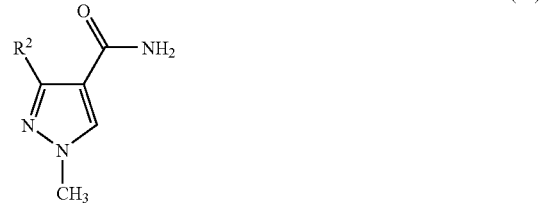

8 Claims, No Drawings

US 7,820,830 B2

PROCESS FOR THE PRODUCTION OF CARBOXANILIDES

This application is a 371 of International Application No. PCT/EP2006/010866 filed Nov. 13, 2006, which claims priority to EP 05024969.7 filed Nov. 15, 2005, the contents of which are incorporated herein by reference.

The present invention relates to a novel process for preparing certain o-cyclopropyl-carboxanilides, which are useful as microbiocides and especially as fungicides.

Various o-cyclopropyl-carboxanilides, methods for their preparation and their use as microbicides are described in WO 03/074491. In one method of preparation an o-cyclopropyl-aniline of the formula (C), shown in Scheme 1 below, where $R^3$ may be, inter alia, a substituted cyclopropyl group, is reacted with an acid chloride of the formula Het-COCl, where Het is for example a substituted pyrazolyl group, to form an o-cyclopropyl-carboxanilide of the formula (D):

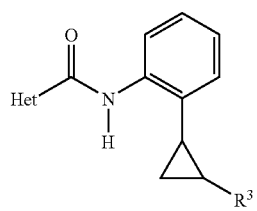

The o-cyclopropyl-aniline (C) is made by a multi-stage process which culminates in the two steps shown in Scheme 1:

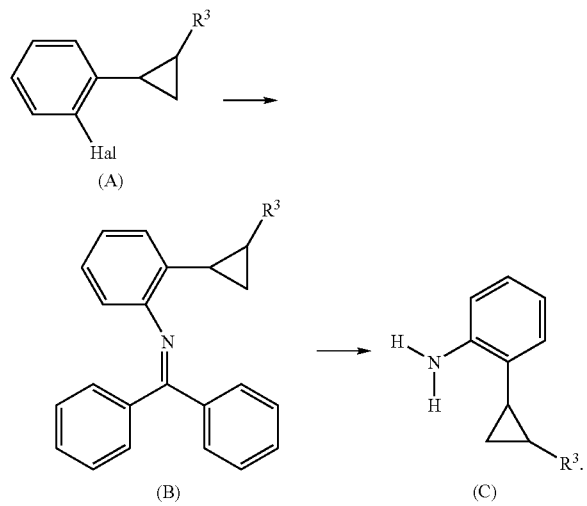

As seen from Scheme 1, this process involves the conversion of a 2-(2-halophenyl)-cyclopropane of the formula (A), where Hal is bromo or iodo and $R^3$ is, as mentioned above, a substituted cyclopropyl group, to the o-cyclopropyl-aniline (C) via the imine (B). The imine (B) is formed by reacting the cyclopropane (A) with benzophenone imine for several hours in a solvent, such as benzene or toluene, at its reflux temperature in the presence of sodium tert-butoxide, tris-dibenzylideneacetone-dipalladium ($Pd_2dba_3$) and racemic 2,2'-bis(diphenyl-phosphino)-1,1'-binaphthyl (BINAP) and then added (usually as a crude, isolated product) to a mixture of hydroxylamine hydrochloride, sodium acetate and a solvent, such as methanol, to form a cis-/trans-mixture of the aniline (C).

This process for preparing o-cyclopropyl-carboxanilides starting from a 2-(2-halo-phenyl)-cyclopropane of the formula (A) is expensive and not well suited to large scale production. Amongst other disadvantages, it involves three separate stages and requires the use of the expensive benzophenone imine and the isolation of the intermediate imine (B). In addition, according to WO 03/074491, the cyclopropane (A) must be a bromo- or iodo-phenyl cyclopropane and not the corresponding, cheaper, but less reactive, chlorophenyl cyclo-propane.

It has now been found that certain o-cyclopropyl-carboxanilides may be prepared directly from a 2-(2-bromo- or 2-chlorophenyl)-cyclopropane in a one-stage process, better suited to, and less costly for, use on a commercial scale.

Thus, according to the present invention, there is provided a process for the preparation of the compound of the general formula (I):

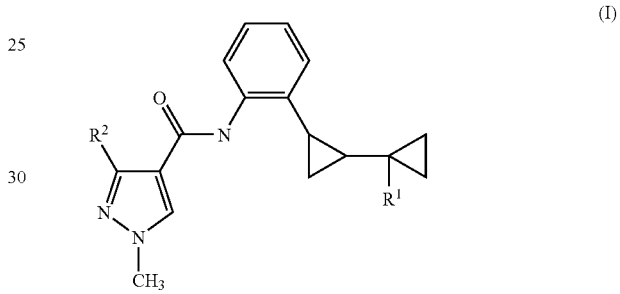

wherein $R^1$ is H or $C_{1-4}$ alkyl and $R^2$ is difluoromethyl or trifluoromethyl, which comprises reacting the compound of the general formula (II):

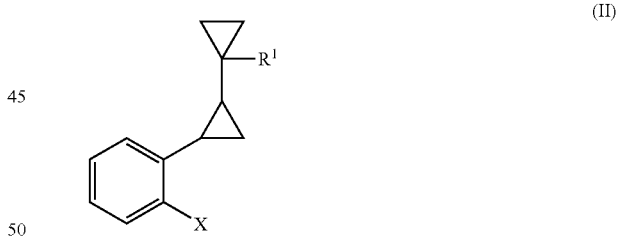

wherein $R^1$ has the meaning given above and X is chloro or bromo (preferably chloro), with a compound of the general formula (III):

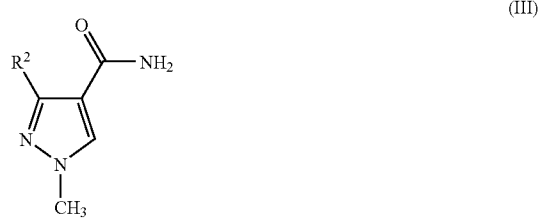

wherein R² has the meaning given above, in the presence of a base, a palladium catalyst and a ferrocenyl biphoshine ligand of the Josiphos type, the reaction being carried out in an ether solvent at a reflux temperature of at least 100° C.

The term "alkyl" mentioned herein refers to branched or unbranched alkyl groups containing from 1 to 4 carbon atoms and is methyl, ethyl, n-propyl, iso-propyl, n-butyl, sec-butyl, iso-butyl or tert-butyl.

The base used in the process of the invention is preferably a strong base, typically an alkali metal or alkaline earth metal hydroxide, carbonate or alkoxide or an alkali metal phosphate or bicarbonate, or mixtures thereof. Particularly suitable are the hydroxides or carbonates of sodium, potassium, cesium, lithium, calcium and barium, the phosphates of sodium and potassium and the $C_1$-$C_4$ alkoxides of sodium and potassium. Of particular interest are potassium tert-butoxide, sodium tert-butoxide, potassium hydroxide, sodium hydroxide, sodium methoxide, sodium ethoxide, sodium carbonate, potassium carbonate, cesium carbonate and potassium phosphate.

The amount of base used will depend on the particular base chosen, but will normally be from 1 to 3, conveniently from 1 to 2 and typically 1.2 to 1.6 moles per mole of compound (II).

The palladium catalyst used in the process of the invention is suitably palladium dichloride, palladium(II) acetate, tris-dibenzylideneacetone-dipalladium ($Pd_2dba_3$) or bis-dibenzylideneacetone palladium ($Pd(dba)_2$). Palladium(II) acetate has been found particularly convenient to use.

The ferrocenyl biphoshine ligand used is of the Josiphos type. Such ligands are commercially available and include:
(R)-(−)-1-[(S)-2-(bis(4-trifluoromethylphenyl)phosphino)ferrocenyl]ethyl-di-tert-butyl-phosphine;
(R)-(−)-1-[(S)-2-(di(3,5-bis-trifluoromethylphenyl)phosphino)ferrocenyl]ethyldicyclohexylphosphine;
(R)-(−)-1-[(S)-2-(di(3,5-bis-trifluoromethylphenyl)phosphino)ferrocenyl]ethyldi(3,5-dimethyl-phenyl)phosphine;
(R)-(−)-1-[(S)-2-(dicyclohexylphosphino)ferrocenyl]ethyldi-tert-butylphosphine;
(R)-(−)-1-[(S)-2-(dicyclohexylphosphino)ferrocenyl]ethyldicyclohexylphosphine;
(S)-(+)-1-[(R)-2-(dicyclohexylphosphino)ferrocenyl]ethyldicyclohexylphosphine;
(S)-(+)-1-[(R)-2-(dicyclohexylphosphino)ferrocenyl]ethyldiphenylphosphine;
(R)-(−)-1-[(S)-2-(bis(3,5-dimethyl-4-methoxyphenyl)phosphino)ferrocenyl]ethyldicyclohexyl-phosphine;
(S)-(+)-1-[(R)-2-(di-furylphosphino)ferrocenyl]ethyldi-3,5-xylylphosphine;
(R)-(−)-1-[(S)-2-(diphenylphosphino)ferrocenyl]ethyldi-tert-butylphosphine;
(S)-(+)-1-[(R)-2-(diphenylphosphino)ferrocenyl]ethyldi-tert-butylphosphine;
(R)-(−)-1-[(S)-2-(diphenylphosphino)ferrocenyl]ethyldicyclohexylphosphine;
(R)-(+)-1-[(R)-2-(diphenylphosphino)ferrocenyl]ethyldicyclohexylphosphine
(S)-(+)-1-[(R)-2-(diphenylphosphino)ferrocenyl]ethyldicyclohexylphosphine;
(R)-(−)-1-[(S)-2-(dicyclohexylphosphino)ferrocenyl]ethyldiphenylphosphine;
(R)-(−)-1-[(S)-2-(diphenyl)phosphino)ferrocenyl]ethyldi(3,5-dimethylphenyl)phosphine;

and racemic mixtures thereof, especially racemic mixtures of 2-(dicyclohexylphosphino)-ferrocenyl]ethyldi-tert-butylphosphine.

Other Josiphos ligands which may be used include:
(R)-(−)-1-[(S)-2-(di-tert-butyl-phosphino)ferrocenyl]ethyl-di-o-tolylphosphine

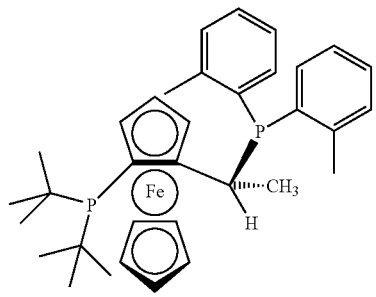

(R)-(−)-1-[(S)-2-(bis(3,5-dimethyl-4-methoxyphenyl)phosphino)ferrocenyl]-ethyl-di-tert-butylphosphine

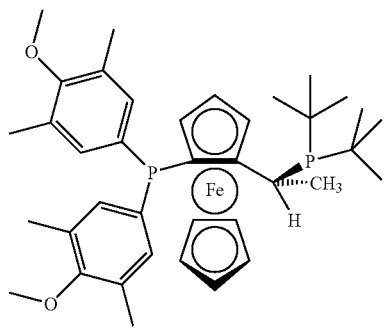

(R)-(−)-1-[(S)-2-(diethylphosphino)ferrocenyl]-ethyl-di-tert-butylphosphine

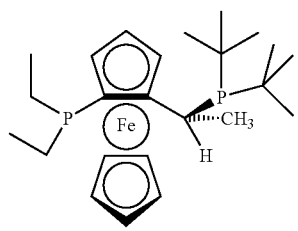

(R)-(−)-1-[(S)-2-(P-methyl-P-isopropyl-phosphino)ferrocenyl]ethyldicyclohexylphosphine

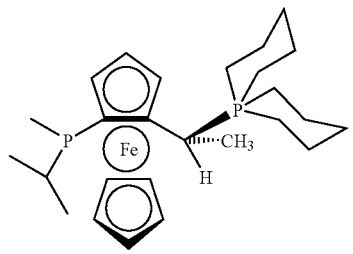

(R)-(−)-1-[(S)-2-(P-methyl-P-phenyl-phosphino)ferrocenyl]ethyl-di-tert-butylphosphine

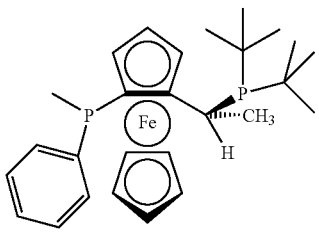

and racemic mixtures thereof, especially racemic mixtures of 2-(di-tert-butylphosphino)-ferrocenyl]ethyl-di-o-tolylphosphine.

A Josiphos ligand which has been found particularly useful is (R)-(−)-1-[(S)-2-(dicyclohexyl-phosphino)ferrocenyl]ethyldi-tert-butylphosphine; which has the structural formula:

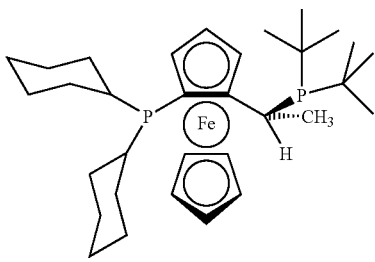

In the invention process, the palladium catalyst will normally be employed in a ratio of from 0.001 to 10 mol %, preferably from 0.01 to 1 and typically about 0.02 mol %, based on compound (II).

The Josiphos ligand will normally be used with one equivalent of the palladium catalyst, or thereabouts.

The solvent used for carrying out the process is an ether solvent, inert under the reaction conditions of the process, having a boiling point such that the reaction mixture can be refluxed at atmospheric pressure at a temperature of at least 100° C. Such solvents include dialkyl ethers of alkylene- and polyalkyleneglycols and, in particular, diethyleneglycol dialkylethers having the general formula:

ROCH$_2$CH$_2$OCH$_2$CH$_2$OR wherein R is C$_{1-4}$ alkyl. Most conveniently, the solvent is di(ethylene glycol) dimethyl ether (diglyme), which has a boiling point of about 162° C.

The process of the invention is carried out at the reflux temperature of the solvent employed, which should be at least 100° C., usually at least 130° C., normally from 130 to 200° C., and typically from 140 to 180° C.

The process may be carried out at atmospheric pressure. The vessel used for the process may be purged with nitrogen before the reactants are introduced, but this is not a requirement.

The 2-chloro- or bromophenyl bicyclopropyl compound (II) used in the process of the invention may exist as a cis- or trans-isomer or a mixture of both. The invention process includes the use of either isomer or any mixture thereof in any proportion and the compound (I) may be obtained as one or other isomer or a mixture of both, accordingly.

The amount of the pyrazole carboxylic acid amide (III) used in the process is conveniently from 1 to 5 moles, for example from 1 to 1.5 moles and typically from 1 to 1.2 moles, for each mole of bicyclopropyl compound (II) used.

The reaction time will depend, inter alia, on the scale of the process and the temperature, but will usually take from 1 to 48 hours, for example, from 6 to 24 hours, and typically from 10 to 20 hours.

The process is conveniently carried out by adding the compounds (II) and (III) with the base, catalyst and ligand to the solvent in a suitable reaction vessel. The order of addition is not critical. When the reaction is adjudged complete, for example, by gas chromatographic analysis of a sample of the reaction mixture, the crude product may be isolated by adding ethyl acetate to the reaction mixture, washing the organic phase with water, drying it and distilling off the solvent. It may then be purified by standard laboratory techniques, for example, by column chromatography.

The product (I) is a useful microbiocide, having especially good fungicidal properties as described in, for example, WO 2003/074491.

The following non-limiting examples illustrate the invention in more detail.

EXAMPLE 1

Preparation of 3-difluoromethyl-1-methyl-1H-pyrazole-4-carboxylic acid (2-bicycloprop-2-yl-phenyl) amide from 2-(2-chlorophenyl)bicyclopropyl using Sodium Tert-Butoxide as Base In a sulfonation flask 2-(2-chlorophenyl)bicyclopropyl (0.58 g; 0.0028 mol; trans/cis mixture ca. 2:1), 3-difluoromethyl-1-methyl-1H-pyrazole-4-carboxylic acid amide (0.5 g; 0.003 mol), sodium tert-butoxide (0.38 g; 0.004 mol), palladium(II) acetate (13 mg; 0.057 mmol) and (R)-(−)-1-[(S)-2-(dicyclohexylphosphino)ferrocenyl]ethyldi-tert-butylphosphine (31 mg; 0.057 mmol) were added to di(ethylene glycol) dimethyl ether (15 ml). The mixture was heated and stirred at its reflux temperature for 16 hours. After cooling, ethyl acetate was added and the organic phase was washed three times with water. After drying and distilling off the solvent in a water jet vacuum a brownish residue remained. This crude product was purified by column chromatography on silica gel (eluant: ethyl acetate/hexane 1:1).

Yield: 0.64 g 3-difluoromethyl-1-methyl-1H-pyrazol-4-carboxylic acid (2-bicycloprop-2-yl-phenyl) amide (68% theory) in the form of a brown solid (trans/cis ratio: ca. 2.7:1).

EXAMPLE 2

Preparation of 3-difluoromethyl-1-methyl-1H-pyrazole-4-carboxylic acid (2-bicycloprop-2-yl-phenyl) amide from 2-(2-bromophenyl)bicyclopropyl using Sodium Tert-Butoxide as Base In a sulfonation flask 2-(2-bromophenyl)bicyclopropyl (0.71 g; 0.0028 mol; trans/cis mixture ca. 2:1), 3-difluoromethyl-1-methyl-1H-pyrazole-4-carboxylic acid amide (0.5 g; 0.003 mol), sodium tert-butoxide (0.38 g; 0.004 mol), palladium(II) acetate (13 mg; 0.057 mmol) and (R)-(−)-1-[(S)-2-(dicyclohexylphosphino)ferrocenyl]ethyldi-tert-butylphosphine (31 mg; 0.057 mmol) were added to di(ethylene glycol) dimethyl ether (15 ml). The mixture was heated and stirred at its reflux temperature for 16 hours. After cooling, ethyl acetate was added and the organic phase was washed three times with water. After drying and distilling off the solvent in a water jet vacuum a brownish residue remained. This crude product was purified by column chromatography on silica gel (eluant: ethyl acetate/hexane 1:1).

Yield: 0.62 g 3-difluoromethyl-1-methyl-1H-pyrazol-4-carboxylic acid (2-bicycloprop-2-yl-phenyl) amide (67% theory) in the form of a brown solid (trans/cis ratio: ca. 2.7:1).

EXAMPLE 3

Preparation of 3-difluoromethyl-1-methyl-1H-pyrazole-4-carboxylic acid (2-bicycloprop-2-yl-phenyl) amide from 2-(2-chlorophenyl)bicyclopropyl using Cesium Carbonate as Base In a sulfonation flask 2-(2-chlorophenyl)bicyclopropyl (0.3 g; 0.0016 mol; trans/cis mixture ca. 2:1), 3-difluoromethyl-1-methyl-1H-pyrazole-4-carboxylic acid amide (0.37 g; 0.0016 mol), cesium carbonate (0.71 g; 0.0022 mol), palladium(II) acetate (7 mg; 0.031 mmol) and (R)-(−)-1-[(S)-2-(dicyclohexylphosphino)ferrocenyl]ethyldi-tert-butylphosphine (18 mg; 0.031 mmol) were added to di(ethylene glycol) dimethyl ether (15 ml). The mixture was heated and stirred at its reflux temperature for 16 hours. After cooling, ethyl acetate was added and the organic phase was washed three times with water. After drying and distilling off the solvent in a water jet vacuum a brownish residue remained. This crude product was purified by column chromatography on silica gel (eluant: ethyl acetate/hexane 1:1).

Yield: 0.27 g 3-difluoromethyl-1-methyl-1H-pyrazol-4-carboxylic acid (2-bicycloprop-2-yl-phenyl) amide (52% theory) in the form of a brown solid (trans/cis ratio: ca. 2:1).

The invention claimed is:

1. A process for the preparation of the compound of the general formula (I):

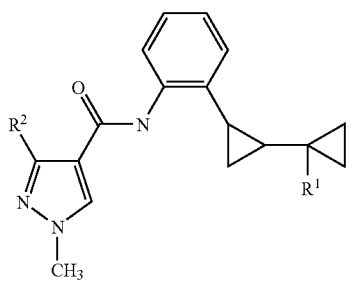

(I)

wherein $R^1$ is H or $C_{1-4}$ alkyl and $R^2$ is difluoromethyl or trifluoromethyl, which comprises reacting the compound of the general formula (II):

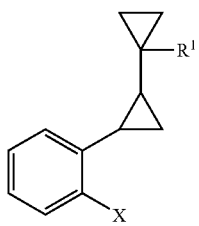

(II)

wherein $R^1$ has the meaning given above and X is chloro or bromo, with a compound of the general formula (III):

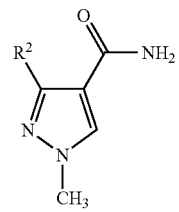

(III)

wherein $R^2$ has the meaning given above, in the presence of a base, a palladium catalyst and a ferrocenyl biphoshine ligand of the Josiphos type, the reaction being carried out in an ether solvent at a reflux temperature of at least 100° C.

2. A process according to claim 1 wherein X is chloro.

3. A process according to claim 1 wherein the base is a hydroxide or carbonate of sodium, potassium, cesium, lithium, calcium or barium, the phosphates of sodium or potassium or the $C_1$-$C_4$ alkoxide of sodium or potassium.

4. A process according to claim 1 wherein the palladium catalyst is palladium dichloride, palladium(II) acetate, tris-dibenzylideneacetone-dipalladium or bis-dibenzylideneacetone palladium.

5. A process according to claim 1 wherein the ligand is (R)-(−)-1-[(S)-2-(dicyclohexylphosphino)-ferrocenyl]ethyldi-tert-butylphosphine having the structural formula:

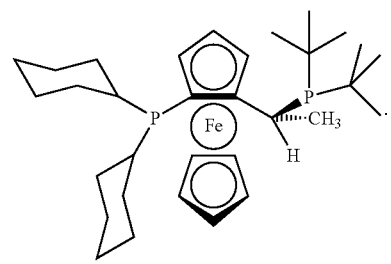

6. A process according to claim 1 wherein the solvent is diethyleneglycol dialkylethers having the general formula:

ROCH$_2$CH$_2$OCH$_2$CH$_2$OR wherein R is $C_{1-4}$ alkyl.

7. A process according to claim 5 wherein the solvent is di(ethylene glycol) dimethyl ether.

8. A process according to claim 1 wherein the reaction is carried out at a temperature of from 130 to 200° C.

* * * * *